(12) United States Patent
Basterash (10) Patent No.: US 12,119,128 B1
(45) Date of Patent: Oct. 15, 2024

(54) NUCLEAR IMAGING DEVICE AND METHOD OF COLLECTING TOMOGRAPHIC PROJECTIONS

(71) Applicant: Jeremy Basterash, Oak Creek, WI (US)

(72) Inventor: Jeremy Basterash, Oak Creek, WI (US)

(*) Notice: Subject to any disclaimer, the term of this patent is extended or adjusted under 35 U.S.C. 154(b) by 0 days.

(21) Appl. No.: 17/531,469

(22) Filed: Nov. 19, 2021

Related U.S. Application Data (60) Provisional application No. 63/117,212, filed on Nov. 23, 2020.

(51) Int. Cl.
| | | |
|---|---|---|
| *G21K 1/02* | (2006.01) | |
| *A61B 6/00* | (2024.01) | |
| *A61B 6/03* | (2006.01) | |
| *A61B 6/42* | (2024.01) | |
| *G06T 1/00* | (2006.01) | |

(52) U.S. Cl.
CPC ............. *G21K 1/025* (2013.01); *A61B 6/037* (2013.01); *A61B 6/4258* (2013.01); *A61B 6/4435* (2013.01); *G06T 1/0007* (2013.01); *G06T 2207/10072* (2013.01); *G06T 2207/30004* (2013.01); *G06T 2211/40* (2013.01)

(58) Field of Classification Search
CPC ..... A61B 6/037; A61B 6/4435; A61B 6/4258; G06T 2207/10072; G06T 2207/30004
See application file for complete search history.

(56) References Cited

U.S. PATENT DOCUMENTS

| | | | |
|---|---|---|---|
| 6,147,352 A * | 11/2000 | Ashburn | A61B 6/037 |
| | | | 250/363.08 |
| 7,470,906 B2 | 12/2008 | Vija | |
| 7,592,597 B2 | 9/2009 | Hefetz et al. | |
| 7,663,111 B2 | 2/2010 | Shahar et al. | |
| 7,671,340 B2 | 3/2010 | Uribe et al. | |
| 7,723,690 B2 | 5/2010 | Uribe et al. | |
| 7,831,024 B2 | 11/2010 | Metzler et al. | |
| 8,487,265 B2 | 7/2013 | Heukensfeldt Jansen et al. | |

(Continued)

FOREIGN PATENT DOCUMENTS

| | | | | |
|---|---|---|---|---|
| DE | 102012203766 A1 * | 9/2013 | ............. | A61B 5/055 |
| DE | 102012213875 A1 * | 2/2014 | ............. | A61B 6/032 |

(Continued)

*Primary Examiner* — David P Porta
*Assistant Examiner* — Casey Bryant
(74) *Attorney, Agent, or Firm* — John Rizvi; John Rizvi, P.A.—The Patent Professor (57) ABSTRACT

A nuclear imaging device that solves continuing problems with existing nuclear imaging systems that are often rendered inoperable because of a detector component failure or a mechanical component failure. The present nuclear imaging device includes a plurality of detectors functioning harmoniously but independently from one another and positionable about a scanning arc. Each detector generally includes a gamma radiation camera, a radiation shield, and a diverging pinhole collimator applicable to the gamma camera. Each pinhole collimator may be positioned a variable distance from the detector to provide zoom in and zoom out optical capabilities that yield higher-quality results and allow for rapid imaging, cutting standard scanning times by more than half.

16 Claims, 5 Drawing Sheets

(56) References Cited

U.S. PATENT DOCUMENTS

| | | | |
|---|---|---|---|
| 9,029,791 | B1 | 5/2015 | Kovalski et al. |
| 9,349,495 | B2 | 5/2016 | Shahar et al. |
| 9,406,412 | B2 | 8/2016 | Lee et al. |
| 10,213,174 | B1 | 2/2019 | Grobshtein et al. |
| 10,502,844 | B2 | 12/2019 | Hugg et al. |
| 2007/0221853 | A1 | 9/2007 | Joung |
| 2007/0238949 | A1* | 10/2007 | Wang .................. A61B 6/0478 600/407 |
| 2013/0324843 | A1 | 12/2013 | Peretz et al. |
| 2014/0037071 | A1* | 2/2014 | Foerner ................ A61B 6/4435 378/193 |
| 2015/0090890 | A1* | 4/2015 | Deller .................. A61B 5/0035 250/363.03 |
| 2015/0335301 | A1 | 11/2015 | Hermony |
| 2015/0366519 | A1* | 12/2015 | Furuta .................. G01T 1/2985 600/431 |
| 2018/0000431 | A1 | 1/2018 | Roth et al. |
| 2019/0209108 | A1* | 7/2019 | Grobshtein ........... G01T 1/1614 |

FOREIGN PATENT DOCUMENTS

| | | | |
|---|---|---|---|
| KR | 101684780 | 12/2016 | |
| WO | WO-03071948 A1 * | 9/2003 | ........... A61B 6/4233 |

\* cited by examiner

NUCLEAR IMAGING DEVICE AND METHOD OF COLLECTING TOMOGRAPHIC PROJECTIONS

CROSS-REFERENCE TO RELATED APPLICATIONS

This application claims the benefit of U.S. Provisional Patent Application Ser. No. 63/117,212, filed on Nov. 23, 2020, which is incorporated herein in its entirety.

FIELD OF THE INVENTION

The present invention generally relates to nuclear imaging devices, and more particularly, to a nuclear imaging device for collecting tomographic projections. The nuclear imaging device allows for targeted and closer scanning proximity to provide quality imaging beyond conventional nuclear imaging devices.

BACKGROUND OF THE INVENTION

Before the revolutionary technique of medical imaging was a common practice among medical practice, physicians resorted to haptic feedback to approximate a possible diagnosis for the symptoms troubling the patient. If the patient needed accurate diagnosis and treatment, such as suffering from a broken bone, development of a tumor, or the swallowing of a foreign object, precision could not be achieved without invasive procedures that often led to complications. Thankfully, just before the turn of the twentieth century, Wilhelm Conrad Roentgen invented an imaging technique that is still widely used today, the x-ray.

The use of the x-ray was rapidly adapted because it provided an image of the inside of the human body, allowing physicians to accurately determine the condition of the patient and propose a treatment option. In principle, ionizing radiation passes through the body and the images were projected on a photosensitive plate placed behind the individual. The downside of this new technology was the amount of radiation that the patient was exposed to, often causing more medical issues than the patient's initial complaint. According to Olaf Langland, the first scientists utilizing this technology establish a dental roentgenological laboratory in 1896, merely a year after its discovery. One of the scientists, Fritz Giesel, later died in 1927 of metastatic carcinoma caused by heavy radiation exposure to his hands. Although this patient—and physician—exposure to radiation was a major downside of the technology, it is still regarded as one of the greatest medical advancements in history.

Imaging technology has only improved with the passage of time. Ultrasounds became the norm to search for tumors and other growths in a non-invasive manner. Following the ultrasound, discovery of magnetic resonance imaging, which uses strong magnet and radio waves to acquire a more detailed image of internal body organs and tissues, became a valuable tool for diagnosis of stroke, cancer, heart disease, etc. Further, the invention of the computed tomography (CT) scan allows for various x-ray measurements to be taken from different angles, creating a detailed final image.

However, there are drawbacks to each of these inventions, with room for improvement. For example, ultrasounds may identify a potential area of concern that is not malignant, due to poor image quality. These false-positive results could lead to more procedures, including biopsies that are not necessary. CT scans produce better quality of images, but at the cost of a high radiation exposure and an uncomfortable and, for some, traumatic experience. According to an article published by St. Michael's Hospital, if contrast is required for the scan, it may take up to 45-60 minutes, without the contrast it takes 15-30 minutes. Further, full system failure with individual component loss occurs with these imaging technologies.

Therefore, there is an unmet need for a medical imaging technology that creates a tomographic reconstruction of sufficient resolution and sensitivity to elicit accurate diagnostic results. Further, a device is needed that lessens the radiation exposure a patient receives during imaging, and the time it takes to obtain an image should be less than what is presently the norm.

SUMMARY OF THE INVENTION

The present invention is directed to a nuclear imaging device that utilizes a plurality of detectors disposed around a specially designed scanning arc. The plurality of detectors operate harmoniously but independently from one another to scan radiating projections emitting from a centralized object, which in many cases may be a person, to produce high quality computed tomography for three-dimensional reconstruction. The positioning of the detectors about the object also allows for the scanning period to be significantly reduced from the standard 12-15 minute period to about 2-4 minutes.

Introducing a first embodiment of the invention, the present invention consists of a nuclear imaging system, comprising;
  a support platform for supporting an object;
  an image capturing device, comprising
    a vertical support member having an upper end and a lower end, the vertical support positionable adjacent to the support platform,
    an extendable arm having a proximal end and a distal end, the proximal end connected at the upper end of the vertical member and extending substantially normal to the vertical member,
    a rotatable imaging arm connected to the distal end of the extendable arm, the image arm including a cavity therein,
    a plurality of detectors installed inside of the cavity, each detector independently operable and capable of moving a detector head forward and backwards relative to a starting position to move substantially close but not touch the object, each detector of the plurality of detectors conforming to the object's exterior profile and capable of capturing data; and
  at least one processor configured to execute programmable instructions stored in memory, to receive the data and create a high quality computed tomography three-dimensional image.

In another aspect, the imaging arm may be positionable substantially close to the object.

In another aspect, the support platform may include a movable upper portion and a movable lower portion.

In another aspect, each detector inside of the imaging arm may be positionable a variable distance from the object when the imaging arm is positioned substantially close to the object, where the plurality of detectors follow and conform to the shape of the object.

In another aspect, the plurality of detectors are arranged inside of the cavity of the imaging arm in three tiers.

In another aspect, the imaging arm comprises an arc-shaped arm.

In another aspect, each tier may include anywhere between about 8 to about 12 detectors.

In another aspect, the three tiers are separated into a top tier of detectors, an intermediary tier of detectors, and a bottom tier of detectors.

In yet another aspect. The top tier of detectors and the bottom tier of detectors are positionable at a vertical angular offset with respect to the intermediary detectors.

In another aspect, the detectors include a front portion that includes the movable head and a rear portion that includes a CZT detector.

In yet another aspect, each one of the top tier detectors is about a positive 5 to about a 6 degree angular offset with respect to the intermediary detectors such that the movable head of the top tier detector is pointing in a slightly downward direction with respect to the movable head of the intermediary tier detector.

In yet another aspect, each one of the bottom tier detectors is about a negative 5 to about a 6 degree angular offset with respect to the intermediary detectors such that the movable head of the bottom tier detector is pointing in a slightly upward direction with respect to the movable head of the intermediary tier detector.

In yet another aspect, the angular offset between the top tier detector and the intermediary detector is a positive 5.625 degrees, and the angular offset between the bottom tier detector and the intermediary detector is negative 5.625 degrees.

In yet another aspect. The top tier of detectors and the bottom tier of detectors are positionable at a horizontal angular offset distance with respect to the intermediary detectors.

In another aspect, the horizontal angular offset distance for the top tier detector is about 5 to about 6 degrees in a first direction with respect to the intermediary tier detector, and the horizontal angular offset distance for the bottom tier detector is about 5 to about 6 degrees in a second direction, opposite the first direction, with respect to the intermediary tier detector.

In yet another aspect, the horizontal angular offset of the top and bottom tier detector is 5.625 degrees.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The instant invention provides a nuclear imaging system providing an arc-shaped imaging arm that includes a plurality of imaging detectors installed therein, and with each detector being independently operable inside of the imaging arm. In one embodiment, the nuclear imaging system is a Single Photon Emission Computed Tomography (SPECT) imaging scanner that includes a plurality of radiation detectors to acquire a SPECT image. One will appreciate that the instant invention described may be utilized in connection with alternative imaging systems, such as Positron Emission Tomography (PET) imaging system. Moreover, the imaging system capable of imaging different objects, including other objects than people.

Figure 1:
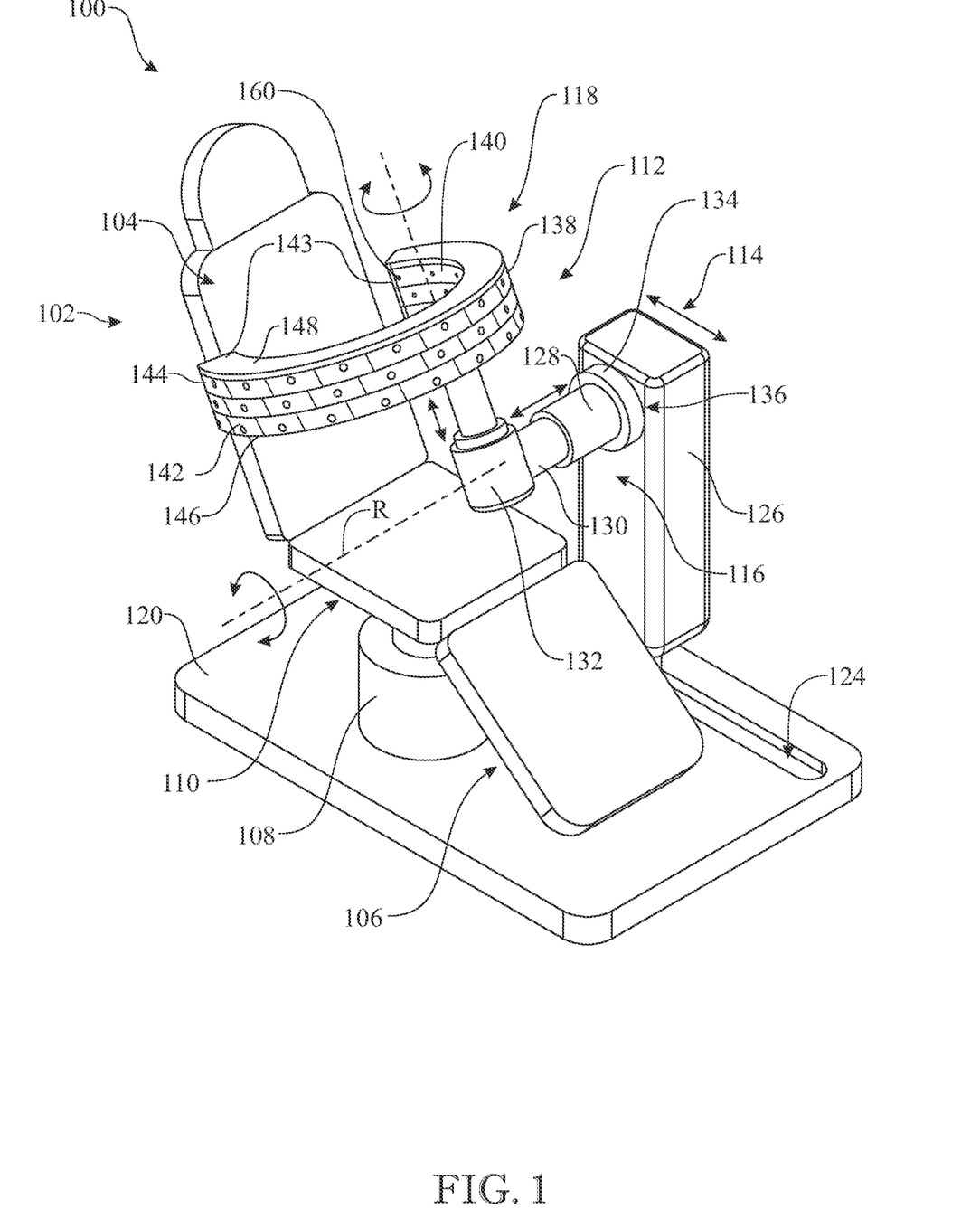
FIG. 1 presents a front perspective view showing a first embodiment of the nuclear imaging device of the present invention.
Figure 2:
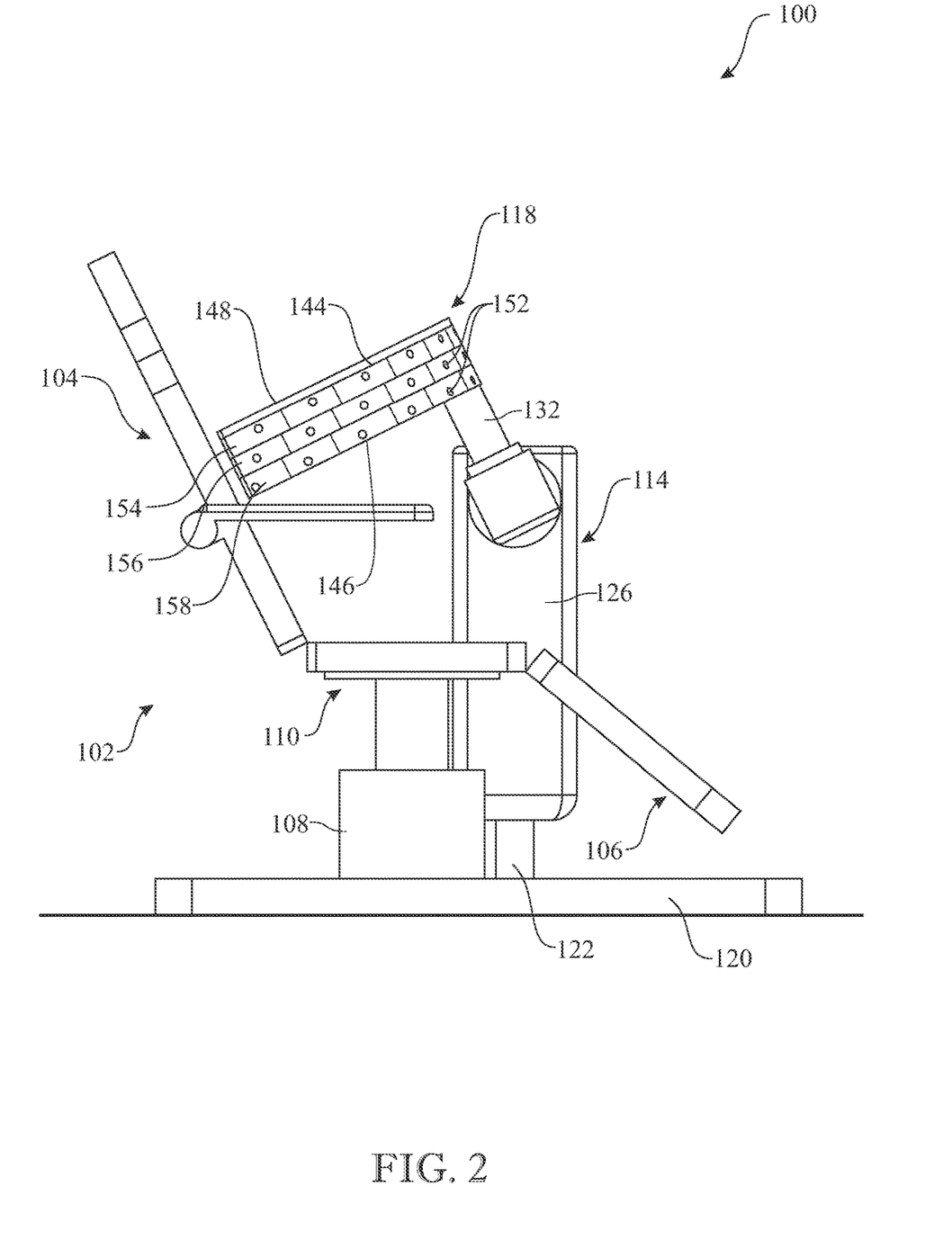
FIG. 2 presents a side-elevation view of the first embodiment of the nuclear imaging device of the present invention.

Referring initially to FIGS. 1 and 2, a nuclear imaging system 100 in accordance with the present invention, is generally shown. The nuclear imaging system 100 comprises a support platform 102. The support platform 102 includes a support member 108 that bears the weight of the support platform. In some instances, the support platform 102 comprises a support member 108 that is supported by a surface 120. In other instances, the support member 108 may be affixed or bolted to the surface 120, if necessary for added security and safety. The support member 108 extends upwardly from the surface 120, connecting with the support platform 102. The support platform 102 is providable in many forms. For example, and as illustrated in FIG. 1, the support platform 102 includes an upper, movable portion 104, an intermediary portion 110, and a lower, movable portion 106. This particular embodiment allows for the support platform 102 to be positionable in a variety of ways. For instance, in one particular embodiment, the upper portion 104 of the support platform may be raised in the upright position in a comfortable angular position, with the lower portion 106 in a slightly downward position. Here, the support platform 102 is positioned to form a reclinable chair. In an alternative embodiment, the upper portion 104 and the lower portion 106 of the support platform is positionable into a horizontal platform, i.e., to form a bed.

Figure 3:
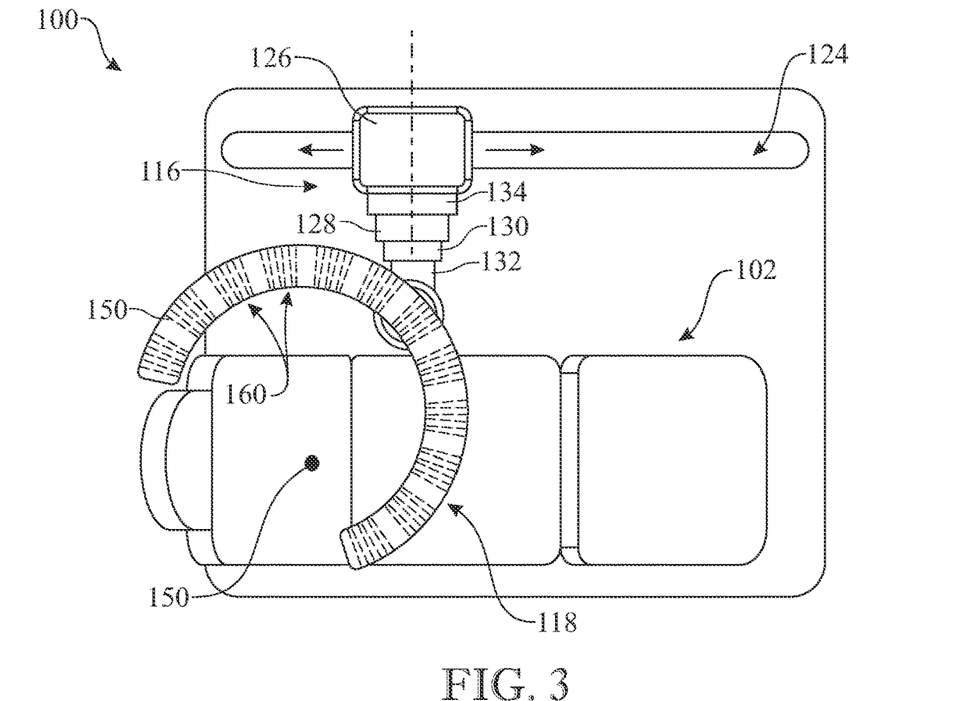
FIG. 3 presents a top plan view showing the range of motion of the nuclear imaging device of the present invention.
Figure 4:
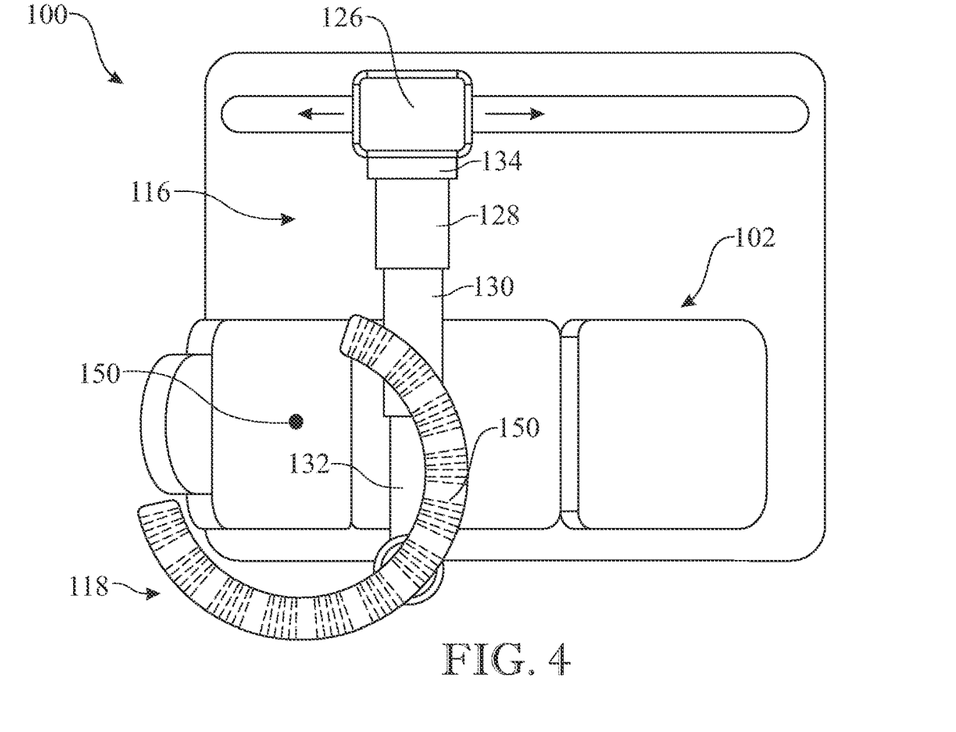
FIG. 4 presents a top plan view of the range of motion of the nuclear imaging device of the present invention.

The nuclear imaging system 100 also includes an imaging device 112. The imaging device 112 generally comprises a vertical support member 114, an extendable arm 116, and an imaging arm 118. We begin with the vertical support member 114, as shown in FIG. 2. The vertical support member 114 includes a first member 122 secured to a track 124 provided on the surface 120 of where the nuclear imaging system 100 is located, and a secondary member 126 coupled to the first member 122. As shown in FIGS. 3 and 4, the track 124 extends parallel to the support platform 102, extending from at least the lower portion 106 of the support platform to at least the upper portion 104 of the support platform 102. In one exemplary embodiment, the first member 122 engaging the track 124 can frictionally slide within the track 124, allowing the positioning and repositioning of the vertical support member 114 without restriction.

Moving the vertical support member 114 about the track 124 can be done in at least two ways. The first one includes mechanical means. In this particular configuration, the track system includes a linear guide, and the first member 122 includes a slidable coupling device, such as a bearing, that engages the linear guide. In this configuration, the vertical support member 114 can be mechanically moved from a first position to a secondary position along the track without any electrical input. A locking mechanism is then usable to lock the position of the vertical support member 114 in place to avoid unwanted movement. In a secondary example, the vertical support member 114 moves about the track 124 via a linear actuator track. In this particular configuration, the first member 122 of the vertical support member 114 is coupled to a linear track, and an electric motor moves the vertical support member 114 about the track 124. Because several alternative modes of implementation are available that would allow the vertical member 114 to translate about track 124, the foregoing is to be considered exemplary and not limiting.

With reference now to FIGS. 1-4, attached to the upper portion of the second member 126 is the extendable arm 116 of the imaging device 112. The extendable arm 116 comprises a plurality of telescoping arms interconnected providing an extendable and retractable arm, as well as rotatable arm about a rotational axis R. As shown in FIG. 1, the extendable arm 116 is attached to the second member 126 of the vertical member 114 in a substantially normal position to the vertical member 114. Put differently, vertical member 114 and the extendable arm 116, when attached to the vertical member, provide a substantially right angle. The extendable arm 116 includes, in this one particular exemplary embodiment, a first arm 128, a second arm 130 connected to the first arm 128, and a third arm 132 connected to the second arm 130, forming a telescopic arm. The first arm 128 of the extendable arm 116 connects to a receiving member 134 on the second member 126 of the vertical support 114. The connection between the telescopic arm 116, mainly where the first arm 128 contacts member 134, is specially done with readily commercially available material so that the stress felt on the extendable arm 116 as it extends, which in turn would magnify the stress felt at the junction point 136 between arm 128 and member 134, does not fail or render the arm inoperable. As is shown in FIGS. 3 and 4, the extendable arm 116 of the nuclear imaging system 100, can retract to at least past one side of the support platform 102 and extendable to at least the other side of the support platform 102, granting a vast range of accessibility to the imaging arm 118.

Turning to FIG. 1, the imaging arm 118 is connected to the extendable arm 116 of the imaging device 112, and in particular, the imaging arm 118 is connected to the third arm 132 of the extendable arm 116. The imaging arm 118 generally comprises an arc-shaped structure. The arc-shaped structure radially spans about an 180 degree arc. The arm 118 comprises a housing 138 having a first exterior sidewall 140, a second exterior sidewall 142, a top end wall 144, a bottom end wall 146, and a pair of ends 143 defining an interior cavity. As is best seen in FIGS. 1 and 3, the first exterior sidewall 140 generally provides a convex curve, different from the second exterior sidewall 142, which generally provides a concave curve. In some embodiments, the top end wall 144 of the imaging arm 118 will include a soft, padded material 148 that comfortably gives way to an external force (e.g., the weight of a person's arms resting on the padded material).

As is best shown in FIG. 1, the imaging arm 118 is rotatably connected to the extendable arm 116 of the imaging device 112 of the nuclear imaging system 100. While the arm is capable of rotating 360 degrees, constraints are implemented so that the open end of the housing 138, which is generally in the shape of an 180 degree arc, is always generally facing in the direction of the upper portion 104 of the support platform 102. The constraints added to the rotational arm of the imaging device 118 are best illustrated in FIGS. 3 and 4. For example, during the use of the nuclear imaging device 100, the imaging arm 118 is positionable at about negative 270 degrees (i.e., 270 degrees counter-clock wise from center), such that the open end of the arm is positionable to face an object's left posterior portion. In instances where the object is a person, the starting position here would be the left posterior oblique of the person. The arm is rotatable about the object 150 resting on the support platform in a clock-wise fashion to about 45 degrees from center, or when it reaches the right anterior oblique of the object. This range of movement is possible through linear and rotational movement of the imaging device 118.

For instance, as shown in FIG. 3, to reach the left posterior oblique of the object 150, the extendable arm 116 of the imaging device 112 fully retracts, and the rotational arm of the imaging arm 118 rotates counter-clock wise until reaching a designated position. To reach the right anterior portion of the object 150, as shown in FIG. 4, the extendable arm 116 extends, and the rotational arm of the imaging arm 118 begins to rotate clock-wise until reaching the designated position. One will appreciate that the combination of linear and rotational motion of the extendable arm 116 and the rotational movement of the imaging arm 118 allows the imaging device 112 to position itself in various positions around the object 150 that is resting on the support platform 102. Linear motion and rotational motion of the imaging device are accomplishable through well-known techniques in the art that include, but are not limited to, electrical means such as actuators or mechanical means.

Turning now to FIGS. 1, 2, and 5-7, inside the housing 138 of the imaging arm 118 are a plurality of detectors 152. The detectors 152 are arranged inside the housing 138 in at least three tiers, a top tier 154, a middle or intermediary tier

Figure 7:
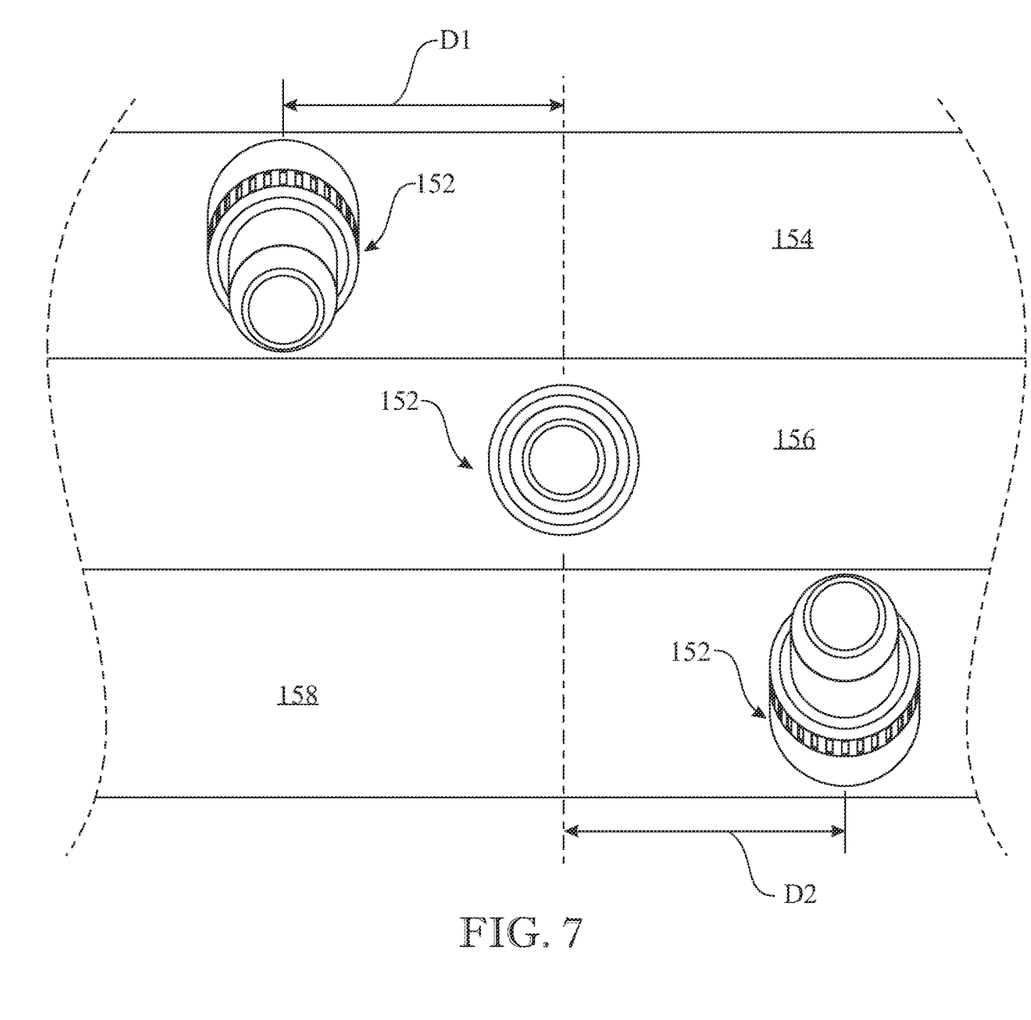
FIG. 7 presents a front side elevation view of the positioning of the imaging cameras installed inside of the imaging arm of the nuclear imaging device of the present invention.

156, and a bottom tier 158. Each tier includes a plurality of detectors 152 equally spaced apart along the arc of the imaging arm 118. As is shown in FIG. 7, a detector 152 in the top tier 154 is a distance D1 offset from the center of a detector in the intermediary tier in a first direction. This is true for all of the detectors in the top tier 154 (i.e., each detector in the top tier being a distance D1 from the detectors in the intermediary tier). The distance D1 between the top tier and the intermediary tier in one exemplary embodiment is about 5 to about 7 degrees, or in some specific embodiments 5.625 degrees apart. Similarly, the bottom tier 158 detectors 152 are a distance D2 offset from the center of the intermediary tier 156 detectors. The distance between the bottom tier and intermediary tier is about 5 to about 7 degrees, or in some specific embodiments 5.625 degrees apart.

In this regard, the distance between each detector in a particular tier, e.g., tier 1, is about 16 to 17 degrees spacially apart along the arc of the imaging arm 118. The detectors 152 in the top tier 154 are offset from center of the vertical plane of the detectors 152 in the intermediary tier 156 in one direction, and the detectors 152 in the bottom tier 158 are offset from center of the vertical plane of the detectors 152 in the intermediary tier 156 in, an opposite, second direction. There is about 9 to about 12 set of detectors in each tier, which amount to a total of about 27 to about 36 detectors in the imaging arm. Each detector 152 is configured to operate independently from the adjoining detector and the detectors below or above it. As such, should one detector fail during the operational use of the nuclear imaging system, the system as a whole would continue to function with the remaining detectors functioning, absent the faulty detector. The capability of using the detectors to obtain data to create an image without the need to stop due to a faulty detector is a significant improvement over existing systems that need to be repaired because of a singular faulty detector before continuing the imaging process.

In addition to the detectors in each tier being separated or spaced apart a set distance, the detectors in the top tier 154 and the bottom tier 158 are at angular offsets from the detectors in the middle tier 156. For instance, as clearly shown in FIG. 6, each detector 152 in the top tier 154 is angularly pitched, such that the rear portion of detector 152 in the top tier 154, where the gamma detector 164 is located, is pointing upwardly, and the movable detector head 160 of the detector is pointing downwardly when compared to the detector 152 in the intermediary tier 164. The angular offset D3 between a detector 152 in the top tier 154 and a detector 152 in the intermediary tier 156 is between about 5 to about 7 degrees, or in specific circumstances 5.625 degrees (negative). Similarly, each detector 152 in the bottom tier 158 is angularly offset from each detector 152 in the intermediary tier 156, such that the rear portion of detector 152 in the bottom tier 158, where the gamma detector 164 is located, is pointing downwardly, and the movable detector head 160 of the detector is pointing upwardly when compared to the detector 152 in the intermediary tier 164. The angular offset D4 between a detector 152 in the bottom tier 154 and a detector 152 in the intermediary tier 156 is between about 5 to about 7 degrees, or in specific circumstances 5.625 degrees (positive).

Figure 5:
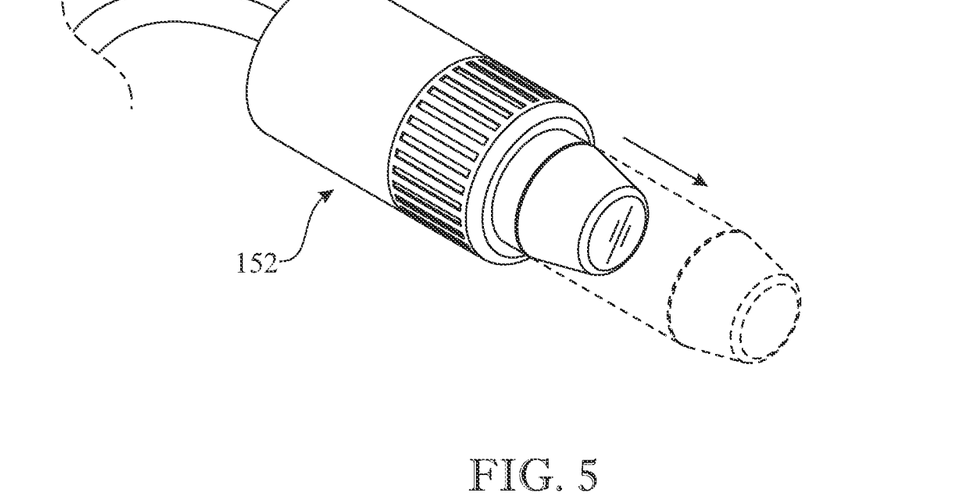
FIG. 5 presents a perspective of the radiation detector or imaging camera installed inside of the imaging arm of the nuclear imaging device of the present invention.

Each detector 152 comprises a detector head 160, a body 162, and a radiation detector 164 (FIG. 5). The head 160 of each detector 152 is facing toward the opening of the arc-shaped housing 138 of the imaging arm 118, which is generally always pointing to the support platform 102. In one exemplary embodiment, the head 160 of the detector 152 comprises a pinhole collimator. One will also appreciate, as shown in FIG. 2, the detector heads or pinhole collimator of each detector 150 match or track the positioning of the upper portion 104 of the support platform 102. Put differently, the housing 138 of the imaging arm where the detectors are installed is kept substantially perpendicular to the upper portion 104 of the support platform 102. As the upper portion 104 of the support platform 102 is repositioned, whether to strategically reposition the object or person on the platform to make the person more comfortable or repositioned to capture a particular image of the person, the imaging arm is also repositioned to maintain that normal substantial perpendicular relationship with the upper portion of the platform.

For instance, if the position of the upper portion 104 of the support platform change 102, and pivot downwardly, to recline the object 150 disposed on the platform 102, the imaging arm 118 would also move and reposition itself so that the plurality detectors 152 inside of the housing 138 of the imaging arm is substantially perpendicular to the backrest of the upper portion 104 of the support platform 102. The repositioning of the imaging arm, in one exemplary embodiment, is done with the help of an electronic device, such as a computer, that connects to the imaging arm. The electronic device connected to the imaging arm may include audio and video circuitry, memory or access to memory, one or more processors, I/O network interface, application program interface, read/write memory (RAM), read-only memory (ROM), writable instructions, and a visual screen or display for navigation.

Figure 6:
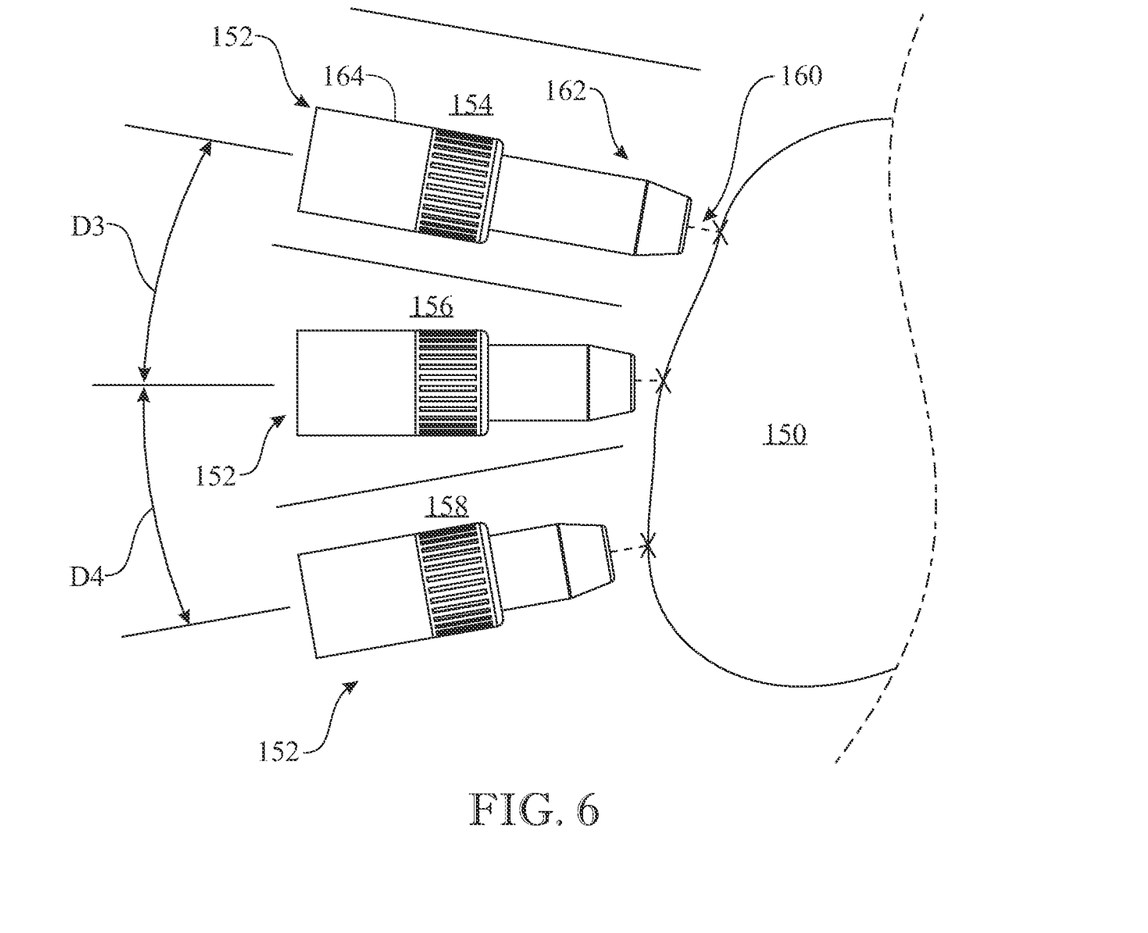
FIG. 6 presents a side elevation view of the positioning of the imaging cameras installed inside of the imaging arm of the nuclear imaging device of the present invention.

With continued reference to FIGS. 1, 3 and 6, the body 162 of the detector 152 is a telescoping body capable of extending and retracting. In an exemplary embodiment, there is roughly about 30 detectors in the imaging arm, and each detector 152 inside the imaging arm 118 is designed and configured to work independently from any other detector 152 in the imaging arm 118. During operational use, the imaging arm 118 is positioned around the object 150 to be scanned. The arc-shaped housing 138 partially envelops the object 150 without touching it. Once the imaging arm 118 is positioned close to the object 150, each detector 152 in each tier, using sensory technology, begins to move and conform to the shape of the object, as seen in FIG. 6. The detectors 152 move close to the object 150 without actually making contact with the object 150. For example, the detectors can move within an inch or half an inch from the object As shown in FIG. 6, if necessary, some detectors retract while others extend until each detector head is within an optimal distance from the object 150 that is being scanned. The movability of the detectors allows a minimum radius and a maximum radius. For example, when the detectors are fully retracted, the imaging arm provides a maximum radius that allows a large object to settle on the support platform. The imaging arm is then positioned around the large object as close as possible before the detectors begin to mobilize and extend toward the object, i.e., reducing the radius. The ability to enlarge and decrease the scan surface area of the imaging arm is also considered to be a considerable advantage over existing systems that cannot accommodate large patients.

Attached to the body 162 of the detector is the radiation or gamma detector 164. The radiation detector 164 of the detector 152 may include a single crystal or multi-crystal, detectors or pixelated detectors or scintillator based detectors that are configured to acquire SPECT image data. In one exemplary embodiment, the detectors is formed from a semiconductor material, such as Cadmium Zinc Telluride, commonly referred to as CZT. In alternative exemplary embodiments, the detector is made from Cadmium Telluride, and silicon, among other non-semiconductor materials. For example, the detector may comprise crystal scintillators, such as Sodium Iodide, Bismuth Germanate, Cerium-Doped Litetium Yttrium Orthosilicate, Cesium Iodide, and Lanthanum bromide, among others.

The imaging device 116 as well as the detectors 152 inside of the imaging arm 118 are controlled through a controller communicating with the electronic device and an imaging system. For example, the imaging system may operate using image reconstruction techniques known in the art to generate tomographic projections, such as SPECT images, of the object that is scanned, which include but is not limited to a person's heart. The image is captured by using the controller to position the imaging arm 118 of the imaging device 116 close to the object 150. While the imaging arm 118 is being positioned, again, it is worth noting that the detectors are fully retracted, providing a maximum radius opening. Once the imaging arm is positioned, say proximate the left posterior oblique of the person, as seen in FIG. 3, the controller is used to manage the movement of the detectors 152. The telescoping body 164 of each detector moves the detecting head 160 of the detector 152 as close as possible to the object without touching the object 150. The radiation emitting from the object is taken in by the detector head 160 and detected by gamma detector 164, which in many instances, is a CZT detector. The radiation detected by each independent detector 152 is considered readable data used to create the tomographic image. Hardware and software, well known in the field, is used to interpret the data received by the detector to create a 3D image.

In summary, the imaging device is capable of acquiring data from an object from a variety of angles simultaneously, diminishing the time required for scanning, thereby reducing the patient's discomfort as well as limiting the amount of time the patient must remain still. Instead of taking the usual 12 to 15 minutes per scan, the instant invention reduces the time needed to scan by more than half or about 2 to about 4 minutes due to its creative design and arrangement of detectors. The imaging device includes an array of identical but relatively independent detectors. Should any one detector fail, the system can remain operable until the faulty detector is repaired at a later time. While the image quality captured will slightly suffer with one fewer detector, the final reconstruction, i.e., image, will remain diagnostically valid.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A nuclear imaging system, comprising:
   a support platform for supporting an object;
   an image capturing device, comprising:
      an arch-shaped imaging arm, the imaging arm extendable and selectively positionable over the object; and
      a plurality of detectors disposed inside of the imaging arm;
      wherein each detector of the plurality of detectors is independently operable and capable of moving a detector head of said each detector relative to a starting position to conform to a shape of the object;
      wherein said each detector of the plurality of detectors is independently capable of capturing and transmitting data; and
      wherein each of the plurality of detectors includes a telescoping body capable of extending and retracting and a rear portion that includes a Cadmium Zinc Telluride detector;
   at least one processor configured to execute programmable instructions stored in memory, to receive the data and create a computed tomography three-dimensional image;
   a base having a track extending parallel to the support platform; and
   a vertical support member engaging the track to allow the translational movement of the imaging capture device along the track;
      wherein the support platform for supporting an object comprises an upper movable portion, an intermediary portion and a lower movable portion;
      wherein the imaging arm is configured to automatically reposition itself to maintain a substantial perpendicular relationship with the upper portion of the platform when the upper movable portion of the platform is repositioned;
      wherein the vertical support member is positioned at a side of the support platform,
      wherein the vertical support member includes a first member secured to the track and a secondary member coupled to the first member;
      wherein the first member secured to the track is configured to frictionally slide within the track, allowing the positioning and repositioning of the vertical support member without restriction;
      wherein the track comprises a linear guide and the first member includes a slidable coupling device configured to engage the linear guide;
      wherein the vertical support member is configured to be mechanically moved from a first position to a secondary position along the track;
      wherein the slidable coupling device comprises a bearing; and
      wherein the system further comprises a locking mechanism configured for use to lock the vertical support member in a position to avoid unwanted movement.

2. The nuclear imaging system of claim 1, wherein the imaging arm is positionable substantially close to the object.

3. The nuclear imaging system of claim 1, wherein each detector is positionable at a distance from the object.

4. The nuclear imaging system of claim 1, wherein the plurality of detectors move to conform to the object's exterior profile.

5. The nuclear imaging system of claim 1, wherein the plurality of detectors are disposed in the imaging arm in at least two tiers.

6. The nuclear imaging system of claim 5, wherein the plurality of detectors are disposed in the imaging arm in three tiers, and each tier includes up to 12 detectors.

7. The nuclear imaging system of claim 5, wherein the imaging arm includes a top tier of detectors, an intermediary tier of detectors, and a bottom tier of detectors.

8. The nuclear imaging system of claim 7, wherein the top tier of detectors and the bottom tier of detectors are positionable at a vertical angular offset with respect to the intermediary detectors.

9. The nuclear imaging system of claim 8, wherein the vertical angular offset of the top tier detectors is about 5 to about 6 positive degrees with respect to the intermediary detectors.

10. The nuclear imaging system of claim 8, wherein the vertical angular offset of the bottom tier of detectors is about 5 to about 6 negative degrees with respect to the intermediary detectors.

11. The nuclear imaging system of claim 1, wherein the arch-shaped imaging arm includes a plurality of detectors disposed in a top tier, an intermediary tier, and a bottom tier, and each detector in the top tier and the bottom tier are offset a horizontal distance of about 5 to about 7 degrees from the detectors in the intermediary tier.

12. A nuclear imaging system, comprising:
a support platform for supporting an object;
an arch-shaped image capturing device, comprising:
 a vertical support member positioned at a side of the support platform;
 an extendable arm connected to the vertical support member,
 an imaging arm connected to the extendable arm, the imaging arm selectively positionable over the object; and
 a plurality of detectors disposed inside of the imaging arm;
  wherein each detector of the plurality of detectors is independently operable and capable of moving a detector head of said each detector relative to a starting position to conform to a shape of the object;
  wherein each detector of the plurality of detectors is independently capable of capturing and transmit data; and
  wherein each of the plurality of detectors includes a telescoping body capable of extending and retracting and a rear portion that includes a Cadmium Zinc Telluride detector;
at least one processor configured to execute programmable instructions stored in memory, to receive the data and create a computed tomography three-dimensional image; and
a base having a track extending parallel to the support platform;
 wherein the vertical support platform is configured to engage the track to allow the translational movement of the image capturing device along the track;
 wherein the support platform for supporting an object comprises an upper movable portion, an intermediary portion and a lower movable portion;
 wherein the imaging arm is configured to automatically reposition itself to maintain a substantial perpendicular relationship with the upper portion of the platform when the upper movable portion of the platform is repositioned;
 wherein the vertical support member is positioned at a side of the support platform;
 wherein the vertical support member includes a first member secured to the track and a secondary member coupled to the first member;
 wherein the first member secured to the track is configured to frictionally slide within the track, allowing the positioning and repositioning of the vertical support member without restriction;
 wherein the track comprises a linear guide and the first member includes a slidable coupling device configured to engage the linear guide;
 wherein the vertical support member is configured to be mechanically moved from a first position to a secondary position along the track;
 wherein the slidable coupling device comprises a bearing; and
 wherein the system further comprises a locking mechanism configured for use to lock the vertical support member in a position to avoid unwanted movement.

13. The nuclear imaging system of claim 12, wherein the plurality of detectors are disposed in the imaging arm in at least three tiers.

14. The nuclear imaging system of claim 13, wherein the imaging arm includes a top tier of detectors, an intermediary tier of detectors, and a bottom tier of detectors.

15. A nuclear imaging system, comprising:
a support platform for supporting an object;
a base including a track extending parallel to the support platform;
an image capturing device, comprising:
 a vertical support member positioned at a side of the support platform, the vertical support member engaging the track extending to allow the translational movement of the imaging capture device along the track;
 an extendable arm connected to the vertical support member;
 an imaging arm having an arch-shaped design connected to the extendable arm, the imaging arm selectively positionable over the object; and
 a plurality of detectors disposed inside of the imaging arm in at least three tiers;
  wherein each detector of the plurality of detectors is independently operable and capable of moving a detector head of said each detector relative to a starting position to conform to a shape of the object;
  wherein each detector of the plurality of detectors is independently capable of capturing and transmitting data;
  wherein the imaging arm includes a top tier of detectors, an intermediary tier of detectors, and a bottom tier of detectors; and
  wherein the top tier of detectors and the bottom tier of detectors are positionable at a vertical and horizontal angular offset with respect to the intermediary detectors; and
at least one processor configured to execute programmable instructions stored in memory, to receive the data and create a computed tomography three-dimensional image;
 wherein the support platform for supporting an object comprises an upper movable portion, an intermediary portion and a lower movable portion;
 wherein the imaging arm is configured to automatically reposition itself to maintain a substantial perpendicular relationship with the upper portion of the platform when the upper movable portion of the platform is repositioned;
 wherein the vertical support member is positioned at a side of the support platform;
 wherein the vertical support member includes a first member secured to the track and a secondary member coupled to the first member;
 wherein the first member secured to the track is configured to frictionally slide within the track, allowing the positioning and repositioning of the vertical support member without restriction;

wherein the track comprises a linear guide and the first member includes a slidable coupling device configured to engage the linear guide;

wherein the vertical support member is configured to be mechanically moved from a first position to a secondary position along the track;

wherein the slidable coupling device comprises a bearing; and wherein the system further comprises a locking mechanism configured for use to lock the vertical support member in a position to avoid unwanted movement.

16. The nuclear imaging system of claim 15, wherein the first member of the vertical support member is coupled to a linear actuator track, the vertical support member is configured to move about the track by the linear actuator track, and an electric motor moves the vertical support member about the track.

* * * * *